(12) United States Patent
Troosters et al.

(10) Patent No.: US 8,700,160 B2
(45) Date of Patent: Apr. 15, 2014

(54) HYPERBOLOID ELECTRICAL CONNECTOR ASSEMBLY

(75) Inventors: Michel Troosters, Dion-Valmont (BE); Claude Berthin, Morienval (FR)

(73) Assignee: Sorin CRM S.A.S., Clamart (FR)

( * ) Notice: Subject to any disclaimer, the term of this patent is extended or adjusted under 35 U.S.C. 154(b) by 180 days.

(21) Appl. No.: 13/120,329

(22) Filed: Mar. 22, 2011

(65) Prior Publication Data

US 2012/0283806 A1 Nov. 8, 2012

Related U.S. Application Data

(63) Continuation of application No. PCT/EP2009/062256, filed on Sep. 22, 2009.

(30) Foreign Application Priority Data

Sep. 24, 2008 (WO) .................. PCT/EP2008/062762

(51) Int. Cl.
*A61N 1/02* (2006.01)

(52) U.S. Cl.
USPC .......................................................... 607/37

(58) Field of Classification Search
USPC ............... 439/843–847; 607/36, 37, 115, 116
See application file for complete search history.

(56) References Cited

U.S. PATENT DOCUMENTS

| | | | | |
|---|---|---|---|---|
| 3,470,527 | A * | 9/1969 | Bonhomme | 439/843 |
| 4,112,953 | A * | 9/1978 | Shanker et al. | 607/37 |
| 5,730,628 | A | 3/1998 | Hawkins | |
| 6,006,135 | A * | 12/1999 | Kast et al. | 607/37 |
| 6,102,746 | A | 8/2000 | Nania et al. | |
| 6,520,998 | B1 * | 2/2003 | Scholler et al. | 439/851 |
| 7,191,518 | B2 * | 3/2007 | Beloritsky et al. | 29/874 |
| 7,305,267 | B2 | 12/2007 | Hector | |
| 7,311,566 | B2 * | 12/2007 | Dent | 439/843 |
| 7,337,002 | B2 * | 2/2008 | Gramse et al. | 607/36 |
| 7,347,746 | B1 | 3/2008 | He | |
| 7,526,339 | B2 * | 4/2009 | Lahti et al. | 607/37 |
| 7,775,841 | B2 * | 8/2010 | Coe et al. | 439/843 |
| 7,850,495 | B2 * | 12/2010 | Niles et al. | 439/843 |
| 8,108,045 | B2 * | 1/2012 | Biggs et al. | 607/37 |
| 2003/0171783 | A1 * | 9/2003 | Tsukamoto et al. | 607/36 |
| 2005/0004615 | A1 * | 1/2005 | Sanders | 607/36 |
| 2006/0167522 | A1 * | 7/2006 | Malinowski | 607/37 |
| 2007/0055319 | A1 * | 3/2007 | Spadgenske | 607/37 |
| 2008/0009912 | A1 | 1/2008 | Spadgenske | |
| 2010/0191299 | A1 * | 7/2010 | Ayzenberg | 607/2 |
| 2011/0264162 | A1 * | 10/2011 | Osypka et al. | 607/37 |

FOREIGN PATENT DOCUMENTS

| | | |
|---|---|---|
| EP | 0587379 | 3/1994 |
| EP | 1638170 | 3/2006 |
| WO | WO 90/02581 | 3/1990 |

* cited by examiner

*Primary Examiner* — Brian T Gedeon
(74) *Attorney, Agent, or Firm* — Foley & Lardner LLP

(57) ABSTRACT

An electrical connector assembly for coupling a first implantable device to a second implantable device, said assembly comprising a male element having one or more male contacts electrically coupled with the first implantable device and a female element comprised of a socket having one or more correspondent female contact electrically coupled with said second implantable device and adapted for receiving said one or more male contact. One or more male contacts are sealed to the male element through a glass or ceramic sealing material. A female contact of said socket comprises a contact structure comprised of a plurality of conductive elongated wires which extend along the internal surface of said the female contact in a hyperboloid arrangement, thereby providing an electrical coupling between the female contact and the corresponding male contact in a plurality of points.

15 Claims, 8 Drawing Sheets

HYPERBOLOID ELECTRICAL CONNECTOR ASSEMBLY

This application is a Continuation of PCT/EP2009/062256 filed Sep. 22, 2009, which in turn claims priority to PCT/EP2008/062762 filed Sep. 24, 2008.

This application is a 371 application of PCT/EP2009/062256, filed Sep. 22, 2009, which, in turn, claims priority of PCT/EP2008/062762, filed on Sep. 24, 2008.

TECHNICAL FIELD

The present invention relates generally to the field of implantable medical devices. More particularly, the invention relates to an electrical connector assembly for connecting implantable medical devices, such as a pacemaker or a neurostimulator for example. However, the invention has also applicability to electrical terminals generally, irrespective of the medical implantable device to which the implantable lead has to be connected.

DESCRIPTION OF RELATED ART

Implantable medical devices are well known in the medical field. Implantable medical devices are generally used for treating particular diseases or disorders in a patient. Examples of such implantable medical devices are: cardiac pacemakers, implantable drug infusion pumps, implantable neurostimulators, defibrillators, cochlear implants and so on.

Typically, implantable devices are subcutaneously inserted in a patient to be treated and are powered either by an internal power source, such as a primary or a secondary battery, or an external power source (that, through the skin of the patient, delivers energy to the implanted device via thin wires) or by means for transcutaneously transferring energy via inductive coupling.

As schematically shown in FIG. 1, an implantable device 1, such as a pacemaker or a neurostimulator, typically comprises a battery 20 and circuitry 30 which are enclosed and sealed in a housing 10 and sends electrical signals to a specific internal part of the human body (e.g. the heart or a nerve) by means of one or more electrodes connected through an implantable lead 70. The housing 10 comprises, according to the prior art, a flat side 80 which is adapted to receive a header 40, the latter comprising a lead receiving channel 50 wherein the implantable lead 70 can be inserted. Said lead receiving channel 50 is electrically connected to circuitry 30 by means of a feedthrough connector 81 through a connection wire 82. In such a way it is possible to establish electrical connection between the implantable device 1 and the implantable lead 70 or with other implanted components such as sensors or an internal antenna for telemetry-based coupling with a second antenna of an external unit. The implantable lead 70 is firmly held within the lead receiving channel 50 by means of a retention means 60, which can be for example a set screw tightened during implantation by means of a torque wrench. Retention means 60 also provides an electrical coupling between the implantable lead 70 and the implantable device 1. In such a configuration, it is essential that housing 10 be protected against the ingress of fluids. The feedthrough connector 81 typically comprises an electrically conducting pin surrounded by insulating material, the insulating material being sealed to the housing 10. The feedthrough connector must remain fluid-tight even when a force is applied to the pin. An example of such an implantable medical device is described in document US 2008/0009912 A1, which describes means for connecting implantable leads 26 to an external header 22 and for connecting the header 22 to the sealed enclosure 24. The sealed enclosure 24 comprises a number of feedthrough terminal pins 74. As discussed in paragraph 27 of this document, the feedthrough terminal pins 74 are connected through crimping and/or welding. Such an implantable device presents the drawback that it is very large in size especially in case a great number of implantable leads are required and it is not, consequently, suitable for applications wherein miniature implantable medical devices are required. Moreover, when connecting header 22 to sealed enclosure 24, the crimping and/or welding is difficult or impossible to perform in operating room conditions and is an irreversible process.

Typically, the materials used to construct the implantable lead must be biocompatible. For providing insulation, common selections are silicone rubber, polyurethane, Teflon, etc. For the conductors, instead, common selections are stainless steel, or platinum and its alloys.

During the implantation of such medical devices within the human body, it may be necessary to establish several electrical connections for correctly installing the medical device. Such electrical connections must be sealed to protect the internal components from the human body's aggressive environment or to prevent undesired electrical signals from passing to surrounding tissue. It is clear, in fact, that any leakage of body fluids or passage of body ions into said housing 10 can result in a deterioration of the medical implantable device.

PRIOR ART DISCUSSION

An example of an electrical connector for an implantable device is disclosed by document U.S. Pat. No. 7,305,267 B2 wherein a proximal end 107 of a lead 110 is plugged into a connector module 106 in order to couple electrodes 22, 24 to an implantable medical device 100. Said connector module 106 comprises a connector bore 120 for hosting said proximal end 107 and a set-screw 127 that, in combination with a threaded connector block 129, serves as an electrical engagement means as well as a secure retention means, when fastened down on said proximal end 107. However, such a connector requires during the implantation the fastening of set-screw 127 by means of assembly tools in order to fix the implantable lead, which is very uncomfortable, difficult, time consuming, especially in operating room conditions, and may cause damages to the connector. Moreover, this connector requires an insertion force which might damage fragile parts (especially insulating parts made up of ceramic or glass) of the module 106. Furthermore, only unipolar or bipolar leads can be connected using this connector.

According to the prior art, electrical contacts between implantable leads and the contacts of an implantable device may also be realized by means of mechanical springs which are located within the connector receptacles of the header, as in the connector described for example in document U.S. Pat. No. 5,730,628 B1. However, a disadvantage of such a solution consists in that these mechanical springs tend to deform permanently and therefore not to assure the necessary contact force and electrical coupling. Moreover this connector requires an insertion force which might cause damages to fragile parts (especially insulating parts of feedthrough connectors made up of ceramic or glass) of the header.

It is also known from document WO 90/02581 A1 a feedthrough connector for implantable device which comprises a barrel assembly 74 (the female connector) which is fitted within the implantable device and has a closed end 76 and an open end 78, the latter which provides a channel wherein receiving an implantable lead 64 having a first contact 66 and a second contact 68. Said first contact 66 and second contacts 68 make electrical contact with a first conductor spring 90 and a second conductor spring 96 respectively. The barrel assembly 74 comprises a first conductive portion 80 (electrically coupled with first conductor spring 90) and a second conductive portion 84 (electrically coupled with second conductor spring 96) separated by nonconductive (ceramic or glass) insulating portions 81, 83, 91, 93. The outer sides of the conductive portions 80, 84 are electrically coupled to the implantable device. No header is used in this design. However, the feedthrough connector described in this document is adapted to be used with standard bipolar pacemaker leads, such as IS-1A, IS-1 or IS-1B leads. As a consequence, this connector is not suitable for miniature implantable devices in the case where leads with multiple contacts are required, since its size would be too large and the manufacture of such a connector would be very complex. Moreover, this connector presents the drawback that the water tightness of the barrel assembly 74 is very difficult to obtain since it requires the melting and fusion of a seal portion with a conductive section. Furthermore, the insertion of the lead 64 within the barrel assembly 74 may produce on the one hand unwanted electrical contacts due to the misalignment between conductive elements (for example, the first contact pin 66 may be in electrical contact with the second spring contact 96) which may cause damages to the implantable device, and on the other hand damages to the conductive portions 80, 84 and/or the non-conductive ceramic portions 81, 83, 91, 93. Another example of a connector assembly without a header is provided by EP0587379. Pin socket 50 and conductive ring 48 of lead 14, connect to conductive pin 22 and ring terminal 24 of receptacle 10, respectively. The insertion of lead 14 in receptacles 10 requires an insertion force, in order to deform spring contacts 28 and 60, and sealing rings 64 and 70. This insertion force may damage glass seals 32, 34, 38 and ceramic insulators 30 and 36. E.g. the sealing ring 64, when in frictional contact with ceramic insulator 30, will submit glass seals 34 and 38, as well as insulators 30 and 36 to a force, and put the integrity of these elements at risk. The assembly of receptacle 10 to housing 80 through brazing or welding is also a source of weakness.

It is also known from document U.S. Pat. No. 5,070,605 B1 a connector for coupling an implantable lead to an implantable device mainly comprising a connector block or header 100 in electrical contact with the implantable device 122. The connector block 100 is provided with a lumen, in which a plurality of rings is linearly arranged. The rings are so sized as to frictionally engage the implantable lead which is provided with a plurality of contacts. This plurality of rings comprises conductive rings which are in electrical contact with the implantable device through feedthrough conductive wires 128 and 130 and which engage with the contacts of the lead. Others rings of said plurality are nonconductive and act as insulators and fluid seals between the conductive rings. However, this connector is not suitable for applications wherein miniature implantable devices are to be coupled with implantable leads having several contacts, since in that case it would be necessary to increase the number of rings which would result in a header too large in size and too complex to be manufactured. Furthermore, the insertion of the lead within the connector block may produce unwanted electrical contacts, similarly to the previous prior art document, which may cause damages to the implantable device. Finally, the insertion force for inserting the lead within the connector block may cause damages to the feedthrough 124 and 126.

It is also known from document WO2008/025159 A1 a connector for implantable device which comprises a male portion 20 and a female portion 30, the latter including a protrusion 37 designed to engage a complimentary recess 27 in the male portion 20. This connector is either connected to an implantable device through cables 12, 13 or through an external header 520. However, this connector presents the drawback that it requires additional elements such as cables 12, 13 or the header 520 which are cumbersome. Furthermore, the engagement of the protrusion 37 within the recess 27 requires an insertion force which may cause damages to the male portion 20. Moreover, the assembly of pins 28 within the male element 20 realized by means of an encapsulating member 26 made up of Epoxy can not provide the high degree of water tightness as required e.g. by the EN 90/385 EU directive—ANNEX 1—Essential Requirements—Art. 9: leakproof, generally validated by application of the MIL-STD-883E leak rate testing with tracer gas (He) at $5.10^{-9}$ cm$^3$/s max. It should be noticed that if the water tightness is to be obtained through other means or materials, this device would be much more complex and larger in size.

The present invention aims at providing a device that overcomes the above-discussed drawbacks of the prior art.

In particular, it is an object of the present invention to provide an electrical connector assembly which simplifies the connection process of a first implantable medical device with another implantable medical device, such as a header or an implantable lead.

Another object of the present invention is to provide an electrical connector capable of providing the mechanical and electrical connection between the implantable device and the header or implantable lead in a less complex manner and using fewer components with respect to the prior art.

More particularly, it is an object of the present invention to provide an electrical connector which is small in size, which has a high degree of reliability of the electrical contacts, and providing a high degree of reliability and water-tightness of the feedthrough connectors. Moreover, such a connector assembly should remain small in size even in case of implantable leads with several contacts.

SUMMARY OF THE INVENTION

According to a first aspect, the invention relates to an electrical connector assembly for coupling a first device to a second device, said assembly comprising a male element having one or more male contacts electrically coupled with said first device and a female element comprising of a socket having one or more correspondent female contact electrically coupled with said second device and adapted for receiving said one or more male contact. Said one or more male contacts are sealed to said male element through a glass or ceramic sealing material. A female contact of said socket comprises a contact structure comprised of a plurality of conductive elongated wires which extend along the internal surface of said female contact in a hyperboloid arrangement, thereby providing an electrical coupling between said female contact and the corresponding male contact in a plurality of points.

Said conductive wires are preferably made of a biocompatible conductive material selected from the group comprising: stainless steel, platinum, gold, or gold plated beryllium copper.

In a first preferred embodiment of the invention, said male element is positioned at a surface of said first device, and said female element is positioned at a surface of said second device. Said second device is then a header adapted for being assembled with said first device.

In a second preferred embodiment of the invention, a receptacle is provided at a surface of said first device, said male element being positioned at the bottom of said receptacle. A matching protrusion is provided at a surface of said second device. The female element is positioned at an extremity of said protrusion. The second device is then a header adapted for being assembled with said first device.

In a third preferred embodiment of the invention, a receptacle is provided at a surface of said first device and the male element is positioned at the bottom of said receptacle. The second device is then a lead, and the socket is adapted to fit into said receptacle.

In this third preferred embodiment, a self-locking means capable of firmly retaining the female element within said receptacle of the male element may be provided.

The female element of second and third embodiment may comprise sealing means for sealing said male contacts and said female contacts from the environment when the electrical coupling between the male element and the female element is established.

The socket has a diameter preferably comprised between 2 and 8 mm.

The female contact has an external diameter preferably comprised between 0.8 and 1.2 mm.

The conductive wires forming the hyperboloid contact structure may have a diameter of 100 µm.

The male contacts are advantageously made of a biocompatible conductive material selected from the group comprising: stainless steel, platinum, gold, or gold plated beryllium copper.

According to a second aspect, the invention relates to first implantable medical device adapted to be coupled to a second implantable medical device, comprising a male element of the electrical connector assembly of the invention.

According to a third aspect, the invention relates to the use of an electrical connector assembly according to the invention for establishing electrical connection between a first implantable medical device and a second implantable medical device.

According to a first aspect, the invention relates to a male element adapted to cooperate in the electrical connector assembly of the invention According to a fifth and last aspect, the invention relates to a female element adapted to cooperate in the electrical connector assembly of the invention.

DETAILED DESCRIPTION OF THE INVENTION

The invention provides an electrical connector assembly for coupling a miniature implantable device to an implantable lead. The assembly comprises a male element having one or more male contact electrically coupled with said miniature implantable device and a female element comprised of a socket having one or more correspondent female contact electrically coupled with said implantable lead and capable of receiving said one or more male contact. The male element is adapted to be fitted within and integral with said miniature implantable device so that it forms a receptacle adapted to receive and fixedly maintain said female element. The male contacts are sealed to the male element through a glass or ceramic sealing material.

Each female contact of said socket comprises a contact structure comprised of a plurality of conductive elongated wires which extend along the internal surface of said female contact in a hyperboloid arrangement, whereby providing an electrical coupling between said female contact and the corresponding male contact in a plurality of points.

The conductive wires are made of a biocompatible conductive material selected from the group comprising for example: stainless steel, platinum, gold, or gold plated beryllium copper.

The electrical connector assembly may comprise self-locking means capable of fixedly retaining the female element within the receptacle of the male element.

The female element may comprise sealing means for sealing said male contacts and said female contacts from the environment when the electrical coupling between the male element and the female element is established.

The socket has a diameter of 5 mm while the female contact has a diameter of 1 mm.

The conductive wires forming the contact structure have a diameter of 100 µm and are made of a biocompatible conductive material selected from the group comprising: stainless steel, platinum, gold, or gold plated beryllium copper.

The invention also provides a miniature implantable medical device adapted to be coupled to an implantable lead. The medical implantable device comprises the male element of the electrical connector assembly of the invention. The miniature implantable device can be a pacemaker or any other implantable stimulator or electronic device.

The electrical connector assembly according to the invention may be used for establishing electrical connection between a miniature implantable device and an implantable lead.

First Embodiment

Figure 1:
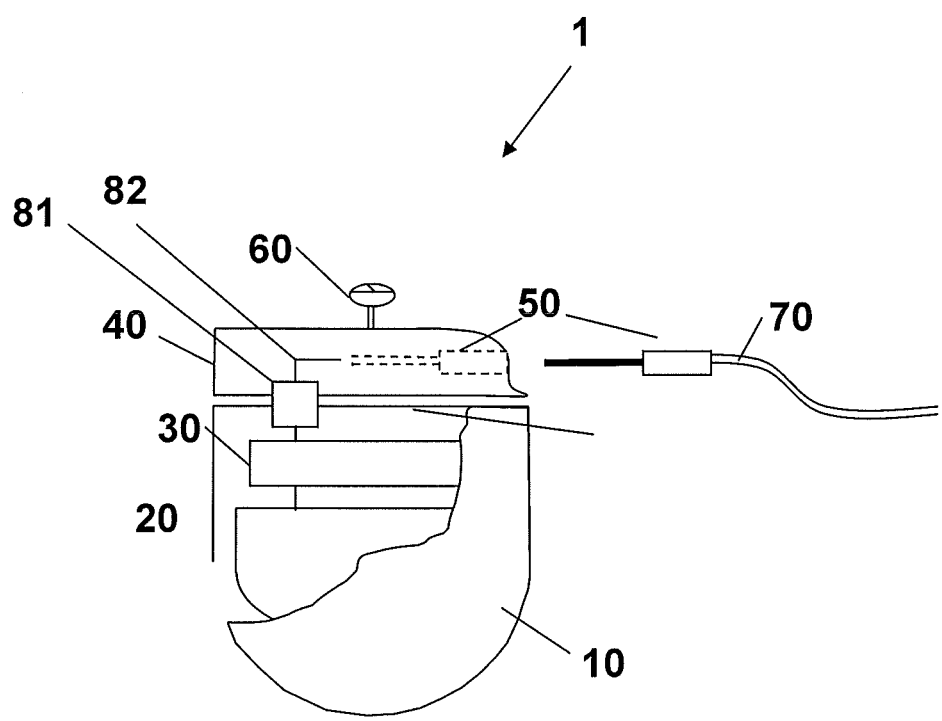
FIG. 1 is a schematic view of an implantable device such as a pacemaker, according to the prior art.
Figure 2A:
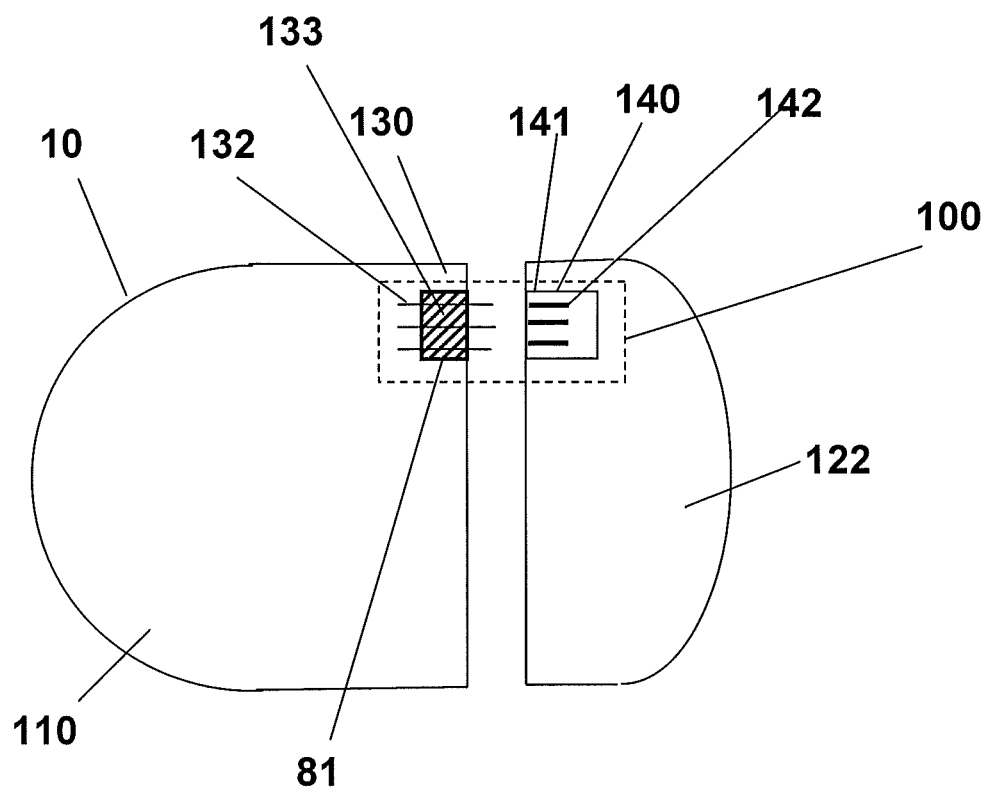
FIGS. 2a, 2b, and 2c are schematic views of implantable medical devices using electrical connector assemblies according to three embodiments of the present invention.

In a first embodiment of the invention represented on FIG. 2a, a housing 10 includes sensitive electronic components which must be protected from body fluids of an implantable medical device 110. Electrical contacts between these electronic components and the outside world are provided by a male element 130 which is a feedthrough connector 81 comprising a plurality of feedthrough pins 132 attached to and electrically insulated from housing 10 through a ceramic or glass material 133. A header 122 comprises a female element 140 which is a socket 141 including a plurality of female contacts 142. The header 122 may provide a connection to an implantable lead or contain equipment such as an antenna. In this embodiment, the assembly of the housing 10 to header 122 is performed in a factory, under controlled clean-room conditions, including positioning means for correctly positioning header 122 in relation to housing 10. The assembly of implantable medical device 110 with header 122 is performed by gluing or any other fastening means such as screws or snap-fit. Gluing is the preferred method because it realizes a water-tight protection of the contact assembly 100.

Second Embodiment

Figure 2B:
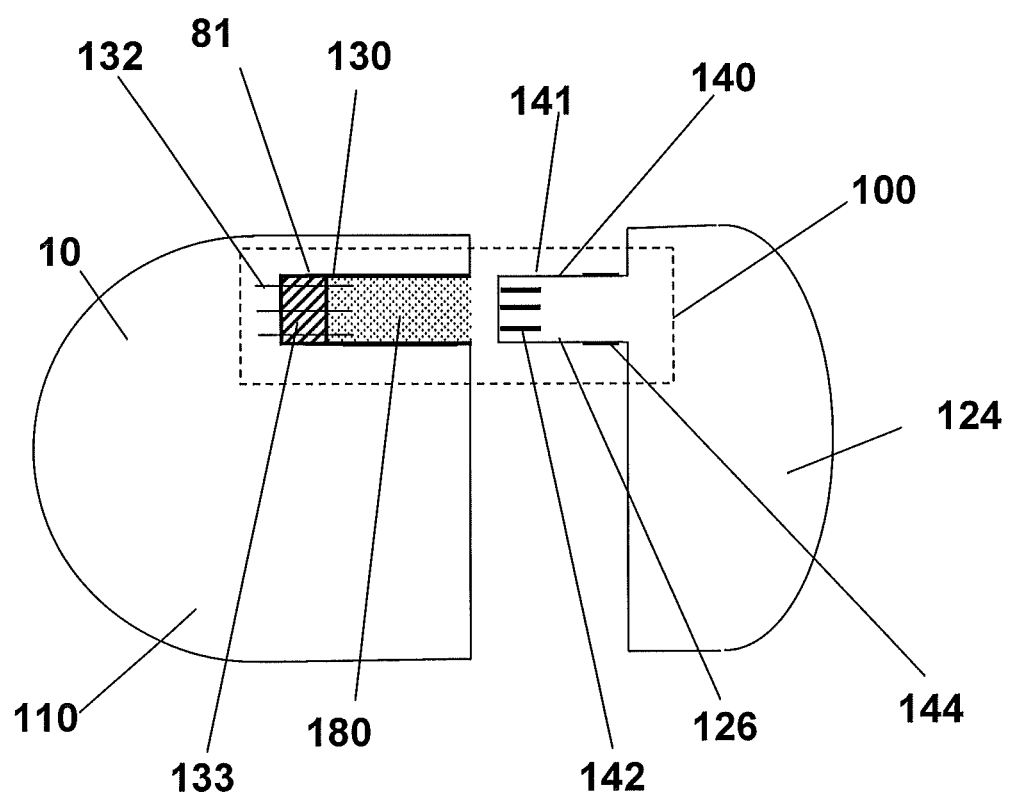

A second embodiment of the invention is represented on FIG. 2b, where corresponding elements have same reference numbers as in FIG. 2a. In this embodiment, the housing is provided with a receptacle 180, having a generally cylindrical shape. The male element 130 is located at the bottom of this receptacle 180. The header 124 is provided with a protrusion 126. The female element 140 is adapted at the extremity of protrusion 126, in such a way that, upon insertion of protrusion 126 into receptacle 180, the feedthrough pins 132 of male element 130 will contact corresponding female contacts 142 of socket 141. In this embodiment, sealing means 144 such as O-rings may be adapted around protrusion 126, which will ensure that no fluid can reach the contacts 132 and 142. Silicone may be used for these seals. It is to be noted that, when inserting protrusion 126 into receptacle 180, the deformation and frictional forces generated by sealing rings are not borne by the ceramic material 133 of the feedthrough connector 81.

Third Embodiment

Figure 2C:
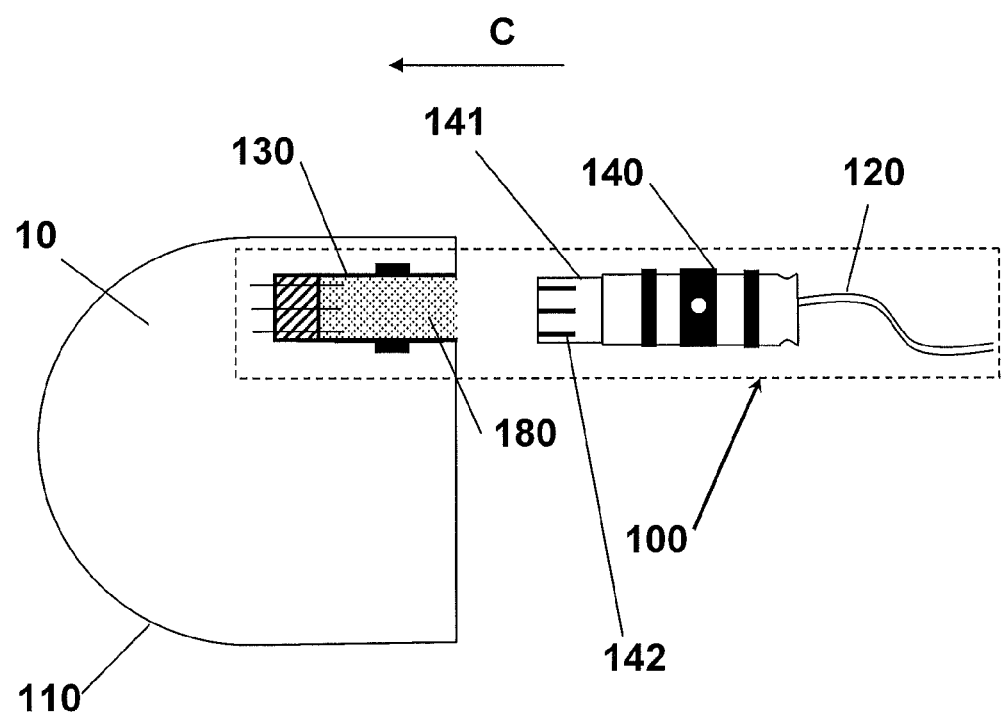

A third embodiment of the invention is represented on FIG. 2c, where also corresponding elements have same reference numbers as in FIG. 2a. In this embodiment, no header is used. Instead, an implantable lead, e.g. for connecting to a nerve cuff or to a heart stimulation electrode, is connected to a socket 141. The socket 141 comprises a plurality of female contacts 142, and the socket 141 is inserted directly into the receptacle 180 of the first implantable device 110. The shape of receptacle 180 and of socket 141 may be designed such that a socket fits only one way into receptacle, and that correct polarisation of the connector assembly is obtained. As in the second embodiment, one or more sealing rings may be provided for ensuring protection of the contacts. With this embodiment, the assembly of the lead to the implantable device 110 may be performed by a surgeon, in operating room condition, without using any special tool, and without risk of fracturing the ceramic material 133 of the feedthrough connector 81. With this third embodiment of the invention, more compact connector assemblies may be produced because no header is used.

Hyperboloid Contact Structure

Hyperboloid electrical contacts are known in the art for having very high reliability, good resistance to vibration, as well as a long durability and are used in aerospace and automotive applications. Hyperboloid contacts are disclosed for example in documents U.S. Pat. No. 4,203,647 B1, US 2002/0037674 A1, or EP 1158620 A1. However, hyperboloid electrical contacts have never been applied to solve the miniaturization requirement problem in human implantable devices. In order to obtain a reliable contact, and avoiding the risks of ceramic or glass fracture when assembling or disassembling connector assemblies, it has been found by the inventors that using hyperboloid electrical contacts in this medical application provided unexpected advantages.

Figure 3:
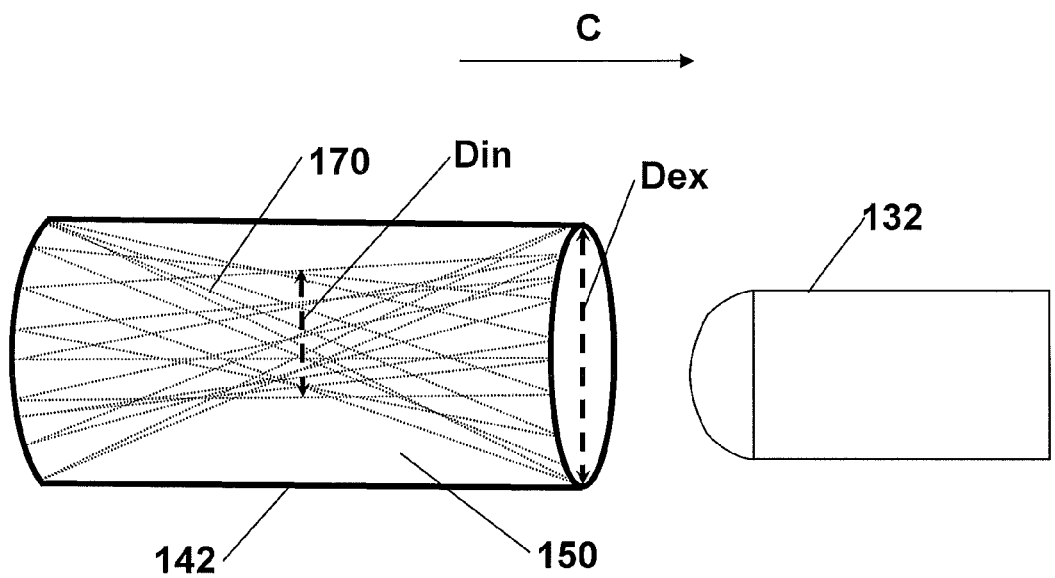
FIG. 3 is a schematic representation of a hyperboloid contact structure.

The contacting structures of all three embodiments of the invention are described by referring to FIG. 3. Each female contact 142 comprises a plurality of conductive linear extended wires 170 which extend longitudinally along the internal region of said female contact 142 and whose the opposite ends are displaced with respect to each other through a small angle around the section (typically circular) of the female contact 142. This particular arrangement forms a hyperboloid structure 150 which acts as a lumen wherein the corresponding feedthrough contact pin 132 of the male element 130 is inserted. It should be noticed that the internal diameter Din of the hyperboloid structure 150 is smaller than the outer diameter Dex, whereby the female contact 142 is capable of fixedly maintaining the corresponding feedthrough contact pins 132 and guaranteeing the electrical contacts into a plurality of points therewith.

Since the use of such a hyperboloid structure 150 only requires a very low insertion force, it is possible to establish the electrical contact without causing damages to the insulating material 133 of the male element 130 neither to the connector socket 141 of the female element 140.

Said female contact 142 has a diameter of 1 mm, while the wires 170 forming the contact structure 150 have a diameter of 100 µm. Wires of the contact structure 150 as well those of the feedthrough pins 132 are made of a biocompatible metal such as stainless steel, platinum, gold, or gold plated beryllium copper. In particular the choice of gold plated beryllium copper is advantageous since this material is much more elastic than other biocompatible metals.

In view of the above, the electrical contact assembly 100 of the invention is perfectly adapted to be used for implantations of miniature medical implantable devices because of its small size as well of the fact that it is adapted to be fitted within and integral with such a miniature implantable device.

Figure 4:
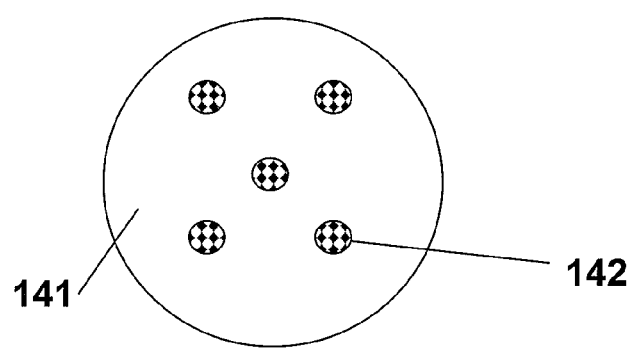
FIG. 4 is an end view of the connector socket of FIG. 2a, 2b or 2c.

FIG. 4 shows the connector socket 141 of the female element 140 viewed along arrow "C" of FIG. 2c. Said connector socket 141 comprises five female contacts 142 and its diameter is 5 mm. However, the number and the location of the female contacts 142 may vary depending on the application. It should be noticed that the connector socket 141 has a high density of contacts and may comprises even more than ten female contacts 142, whereby it is possible to establish electrical coupling with leads having a larger number of contacts with respect to conventional bipolar leads of the prior art without increasing the dimension of the connector assembly 100. For a connector having two contacts 142, the diameter may be as small as 2 mm. For a connector having twelve contacts 142, a larger diameter such as 8 mm may be necessary.

Locking Mechanism

Figure 5:
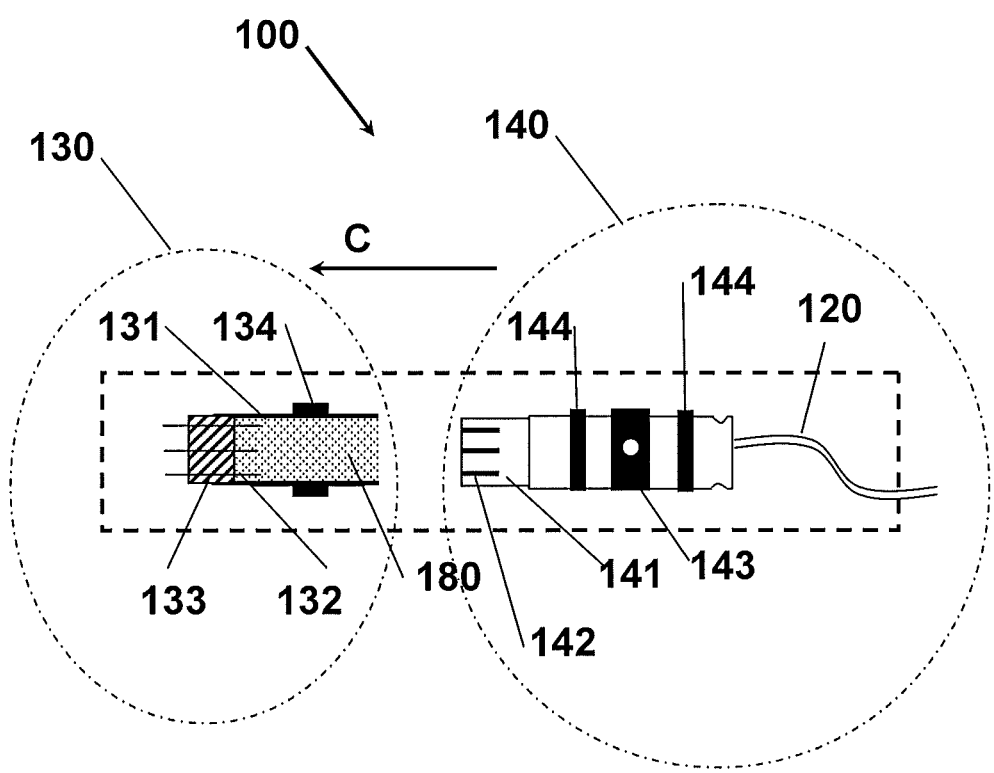
FIG. 5 is a more detailed view of the electrical connector assembly of FIG. 2c.

As schematically shown in FIG. 5, the electrical connector assembly 100 comprises a male element 130 and a female element 140. The female element 140 is adapted to be inserted within the male element 130. The male element 130 comprises a cylindrical frame 131 which forms a receptacle 180 for receiving the female element 140 and feedthrough contact pins 132. These feedthrough contact pins 132 are maintained within the male element 130 and sealed from the internal part of the implantable device 110 by means of an insulating material 133 made up of ceramic or glass. The frame 131 further comprises a groove 134 formed inside the receptacle 180 for operating together with a self-locking means 143 of the female element 140 in order to fixedly retain the female element 140 within the male element 130, as further described. The female element 140 is electrically coupled with the implantable lead 120 and comprises a connector socket 141 with one or more female contacts 142 and has a complementary shape with respect to the cylindrical frame 131 of male element 130 so that it can be easily inserted within the male element 130 in the receptacle 180. The female element 140 further comprises sealing means 144 which consists in rings made up of silicone which are provided to tightly engage the female element 140 within the male element 130 and to seal the connector assembly 110 from the environment once the connection between the male and female elements 130, 140 has been established.

Figure 6:
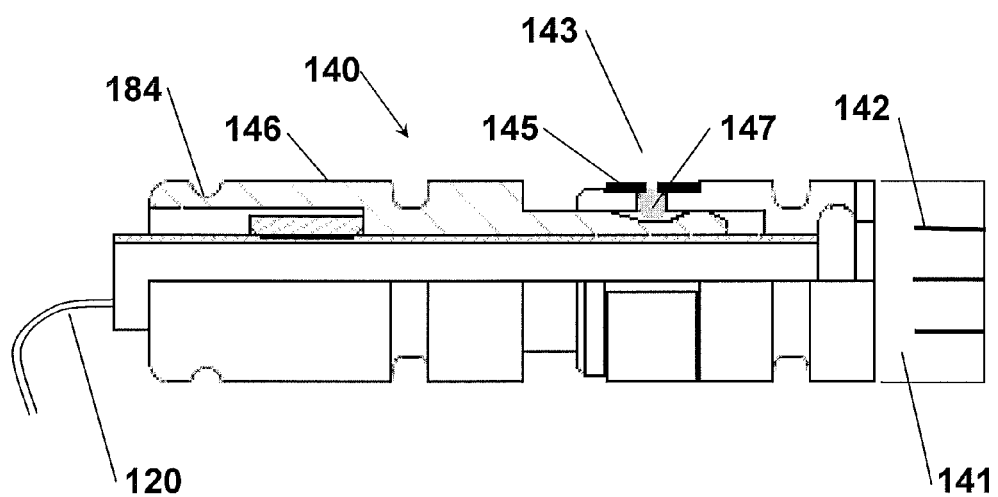
FIG. 6 is a schematic sectional view of the female element of the electrical connector assembly of FIG. 5.

By referring to FIG. 6, the female element 140 further comprises self-locking means 143 which comprises an expandable ring 145 made up of stainless steel which is wrapped around the surface of female element 140, a sliding member 146 and a rigid metallic ball 147. The expandability of said ring 145 is obtained by means of an opened section of said ring 145 which creates two separated portions of the rings 145 that are capable of radially expanding by the rigid ball 147. The ring 145 further comprises an opening for receiving a portion of the ball 147 so as to maintain the ball 147 in a fixed position with respect to the ring 145.

Figure 7A:
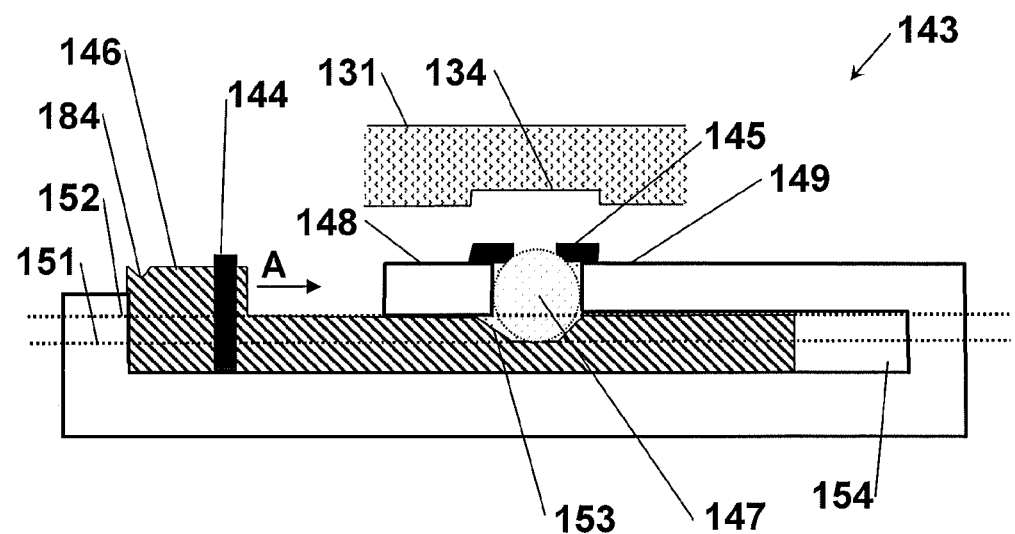
FIG. 7a and FIG. 7b show schematic sectional views of the self-locking means of the female element of FIG. 6.

We refer now to FIG. 7a. When the female element 140 is inserted within the receptacle 180 of the male element 130, it is possible to slide the sliding member 146 in the direction of arrows A within an empty portion 154 of the female element 140. When the sliding member 146 slides in the direction of arrow A, the rigid ball 147 is on the one hand maintained by elements 148, 149 of the female element 140 and by the opening of the ring 145 so that it cannot move laterally, while on the other hand it is gradually elevated in the direction of arrow B whereby passing from a lower level 151 to an upper level 152. The elevation of the rigid ball 147 is caused by the fact that when the sliding member 146 slides along the direction of arrow A, the rigid ball 147 is forced to climb up the inclined profile 153 of the sliding member 146. When the rigid ball 147 is on the lower level 151 the self-locking means 143 is accordingly in an unlocked position, while when it is on the upper level 152, the self-locking means 143 is in a locked position.

Figure 7B:
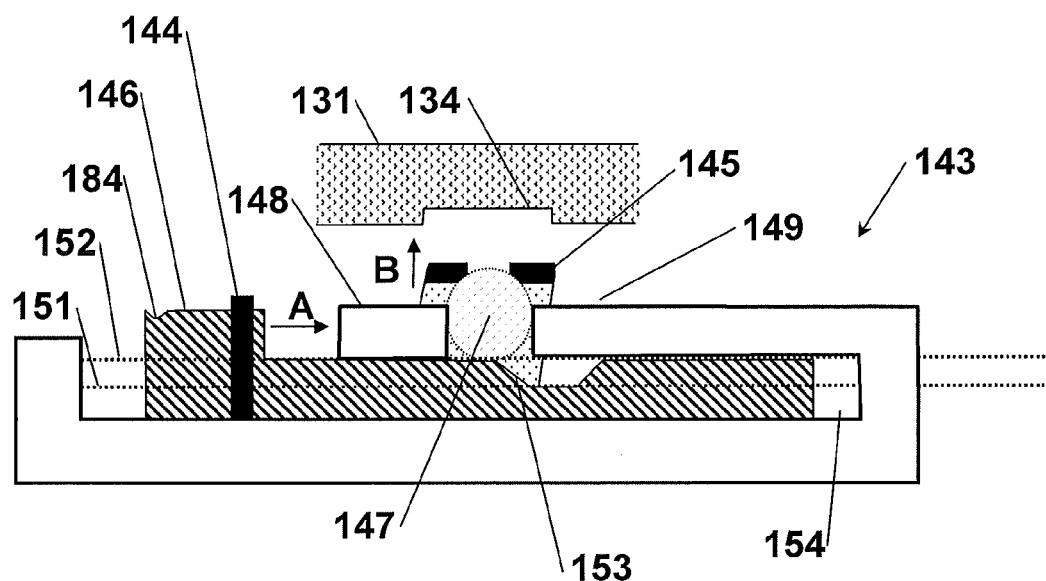

As shown in FIG. 7b, when the rigid ball 147 reaches the upper level 152, it causes the two separated portions of the ring 145 to expand and consequently enter the corresponding groove 134 of the male element 130 so that the female element 140 is mechanically blocked within the receptacle 180 of the male element 130. When the self-locking means is in locked position, the sliding member 146 is firmly kept in place due to the adherence of sealing means 144 against the internal surface of the receptacle 180 so as to prevent the sliding member 146 from freely sliding.

The removal of the female element 140 from the male element 130 can be easily performed by means of a surgical pliers which allows gripping a cavity 184 of the sliding member 146 and sliding it in the reverse direction of arrow A so as the ball 147 gradually passes from the upper level 152 to the lower level 151 (the rigid ball 147 goes down the inclined profile 153 of the sliding member 146). As a consequence, the ring 145 returns to the position shown in FIG. 7a and the female element 140 can easily exit the male element 130.

The self-locking means 143 is extremely resistant to vibration and can resist to traction forces higher than 10 N, as verified by the Applicant. Moreover, the insertion force as well as the extraction force (when the self-locking means 143 is in an unlocked position) is less than 14 N as required by IS-1 regulation. The high reliability of the self-locking means 143 therefore prevents all unwanted disconnections between the female element 140 and the male element 130 of the connector assembly 100 and requires, by contrast, very low insertion/extraction force.

The terms and descriptions used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated. As a consequence, all modifications and alterations will occur to others upon reading and understanding the previous description of the invention. In particular, dimensions, materials, and other parameters, given in the above description may vary depending on the needs of the application. More specifically, a first medical device may be connected to one or more second medical devices through same or different combinations of the connector assembly of the invention.

The invention claimed is:

1. An electrical connector assembly for coupling a first implantable medical device to a second implantable medical device, said assembly comprising
   a male element comprising a feedthrough connector and having one or more male contacts electrically coupled with said first implantable medical device and
   a female element comprising a socket having one or more correspondent female contacts electrically coupled with said second implantable medical device and adapted for receiving said one or more male contacts,
   wherein the one or more male contacts are feedthrough pins and are sealed to said male element through a glass or ceramic sealing material and wherein a female contact of said socket comprises a contact structure comprised of a plurality of conductive elongated wires which extend along the internal surface of said female contact in a hyperboloid arrangement, thereby providing an electrical coupling between said female contact and the corresponding male contact in a plurality of points.

2. The electrical connector assembly according to claim 1 wherein said conductive wires are made of a biocompatible conductive material selected from the group consisting of: stainless steel, platinum, gold, and gold plated beryllium copper.

3. The electrical connector assembly according to claim 1 wherein said male element is positioned at a surface of said first device, and said female element is positioned at a surface of said second device, said second device being a header adapted for being assembled with said first device.

4. The electrical connector assembly according to claim 1 wherein a receptacle is provided at a surface of said first device, said male element being positioned at the bottom of said receptacle, and where a matching protrusion is provided at a surface of said second device, said female element being positioned at an extremity of said protrusion, said second device being a header adapted for being assembled with said first device.

5. The electrical connector assembly according to claim 1 wherein a receptacle is provided at a surface of said first device, said male element being positioned at the bottom of said receptacle, said second device being a lead, said socket being adapted to fit into said receptacle.

6. The electrical connector assembly according to claim 5 further comprising self-locking means capable of firmly retaining the female element within said receptacle of the male element.

7. The electrical connector assembly according to claim 4 wherein said female element comprises sealing means for sealing said male contacts and said female contacts from the environment when the electrical coupling between the male element and the female element is established.

8. The electrical connector assembly according to claim 1 wherein said socket has a diameter from 2 mm to 8 mm.

9. The electrical connector assembly according to claim 1 wherein said female contact has an external diameter (Dex) from 0.8 mm to 1.2 mm.

10. The electrical connector assembly according to claim 1 wherein said conductive wires forming said contact structure have a diameter of 100 μm.

11. The electrical connector assembly according to claim 1 wherein said male contacts are made of a biocompatible conductive material selected from the group consisting of: stainless steel, platinum, gold, and gold plated beryllium copper.

12. A first implantable medical device adapted to be coupled to a second implantable medical device via an electrical connector assembly comprising a male element of the electrical connector assembly according to claim 1.

13. A method for establishing electrical connection between a first implantable medical device and a second implantable medical device comprising the step of:
   providing an electrical connector assembly according to claim 1 between the first and second implantable medical device.

14. An element adapted to cooperate in the electrical connector assembly for coupling a first device to a second device comprising:
   a male element according to claim 1.

15. An element adapted to cooperate in the electrical connector assembly for coupling a first device to a second device comprising:
   a female element according to claim 1.

* * * * *